United States Patent [19]
Marko

[11] Patent Number: 5,777,145
[45] Date of Patent: Jul. 7, 1998

[54] REMOVAL OF CHLOROCARBONS FROM ORGANOCHLOROSILANES

[75] Inventor: Ollie William Marko, Carrollton, Ky.

[73] Assignee: Dow Corning Corporation, Midland, Mich.

[21] Appl. No.: 934,306

[22] Filed: Sep. 19, 1997

[51] Int. Cl.$^6$ ................................................ C07F 7/20
[52] U.S. Cl. .................................................... 556/466
[58] Field of Search ........................................ 556/466

[56] References Cited

U.S. PATENT DOCUMENTS

| | | | |
|---|---|---|---|
| 4,127,598 | 11/1978 | McEntee | 260/448.2 E |
| 4,774,347 | 9/1988 | Marko et al. | 556/466 |
| 4,956,486 | 9/1990 | Marko et al. | 556/466 |
| 5,138,081 | 8/1992 | DeVries et al. | 556/466 |

FOREIGN PATENT DOCUMENTS

| | | |
|---|---|---|
| 50-39649 | 12/1975 | Japan. |
| 59-137312 | 8/1984 | Japan. |
| 6-340560 | 12/1994 | Japan. |

*Primary Examiner*—Paul F. Shaver
*Attorney, Agent, or Firm*—Melvin D. Fletcher

[57] ABSTRACT

A process for reducing the chlorocarbon content of a mixture comprising an organochlorosilane, a chlorocarbon, and a hydrosilane. The process comprises contacting a mixture comprising as a major portion an organochlorosilane and as a minor portion a chlorocarbon and a hydrosilane with an alumina-zirconia cogel to effect formation of a mixture having reduced chlorocarbon content. When the mixture is contacted with the alumina-zirconia cogel the chlorocarbon reacts with the hydrosilane to form a hydrocarbon that is easily separated from the organochlorosilane. The process improves chlorocarbon removal efficiency while maintaining high throughput rates.

15 Claims, No Drawings

REMOVAL OF CHLOROCARBONS FROM ORGANOCHLOROSILANES

BACKGROUND OF INVENTION

The present invention is a process for reducing chlorocarbon content of a mixture comprising an organochlorosilane, a chlorocarbon, and a hydrosilane. The process comprises contacting a mixture comprising as a major portion an organochlorosilane and as a minor portion a chlorocarbon and a hydrosilane with an alumina-zirconia cogel to effect formation of a mixture having reduced chlorocarbon content.

High purity organohalosilanes are needed for the increasing quality requirements in the industrial manufacture of other organosilanes and polyorganosiloxanes. From the direct reaction of an organic halide with silicon is formed a crude organohalosilane mixture containing organohalosilanes and a spectrum of chlorocarbon impurities. The chlorocarbons, in many cases, have boiling points near those of the desired organohalosilanes and can not be separated by commonly used distillation practices. As impurities in the organohalosilanes, chlorocarbons can serve as latent sources of ionic chloride. Ionic chloride can create stability problems in hydrolysis intermediates formed from the organohalosilanes. This problem has been found to exist even when organic chlorides are present at parts per million in the organohalosilanes precursors to these hydrolysis intermediates. Therefore, a process that is effective in reducing chlorocarbons, even at these low levels, is desirable.

Mc Entee, U.S. Pat. No. 4,127,598, describes a process for removing chlorinated biphenyl impurities from impure phenylchlorosilanes with an absorbent bed. The adsorbent bed is selected from a class consisting of a molecular sieve bed and a charcoal bed.

Motomiya, Japanese patent publication No. 50-39649, published Dec. 18, 1975, describes a method for separating olefinic compounds and saturated compounds having a branching tertiary carbon from crude organohalosilanes. The process describes selectively polymerizing the hydrocarbon compounds when they are contacted with a Lewis acid or a metal hydroxide which can become a Lewis acid. The polymerized hydrocarbon compounds are separated from the organohalosilanes by distillation. The presence or removal of chlorocarbons is not discussed by Motomiya.

Clay et al., Japanese Patent Publication No. 59-137312, published Aug. 7, 1984, disclose a method for purification of chlorosilanes in which chlorohydrides of elements from Group III or IV of the periodic table are contacted with chlorine to convert these chlorohydride impurities to chlorides to facilitate separation from the desired chlorosilanes by distillation. No mention is made of applying this method to the removal of chlorocarbon materials from organohalosilanes.

Marko et al., U.S. Pat. No. 4,774,347, teach a process for reducing the chlorocarbon content of alkylsilanes. The process comprises contacting a crude mixture comprising alkylsilanes and containing as a minor portion chlorocarbons and a hydrogen-containing silane with a catalyst that facilitates the reaction of the chlorocarbons with the hydrogen-containing silane to convert the chlorocarbons to an alkane. Disclosed is that alumina may be a useful catalyst in the process and that during the process some rearrangement of more highly alkylated silanes with other alkylhalosilanes may occur. The process can be run at a temperature within a range of about 25° C. to less than 150° C.

Marko et al., U.S. Pat. No. 4,956,486, teach a process for reducing residual organic chlorides in a crude phenylchlorosilane mixture. The process involves contacting the organic chloride with a Lewis acid forming material in the presence of a phenyl source. The phenyl source can be the phenylchlorosilanes and other sources of phenyl present in the crude phenylchlorosilane mixture. The organic portion of the organic chloride forms a hydrocarbon adduct with the phenyl source that allows the hydrocarbon adduct to be easily separated from the phenylchlorosilane mixture.

Morikawa, Japanese Patent Application No. 06340560, describes a method for preparing an oxyhydrochlorination catalyst containing copper chloride as a first component, and a double oxide of zirconium and at least one metal selected from a set consisting of Cu, Fe, Ni, Al, and rare earth metals as a second component.

SUMMARY OF INVENTION

The present invention is a process for reducing chlorocarbon content of a mixture comprising an organochlorosilane, a chlorocarbon, and a hydrosilane. The process comprises contacting a mixture comprising as a major portion an organochlorosilane and as a minor portion a chlorocarbon and a hydrosilane with an alumina-zirconia cogel to effect formation of a mixture having reduced chlorocarbon content. When the mixture is contacted with the alumina-zirconia cogel, the organic portion of the chlorocarbon reacts with the hydrosilane to form a hydrocarbon that is easily separated from the organohalosilane. The process increases chlorocarbon removal efficiency while maintaining high throughput rates.

DESCRIPTION OF INVENTION

The present invention is a process for reducing the chlorocarbon content of a mixture comprising an organochlorosilane. The process comprises contacting a mixture comprising as a major portion an organochlorosilane described by formula

where each R is an independently selected hydrocarbon comprising one to about 20 carbon atoms and $a=0$ to 4 and as a minor portion a chlorocarbon and a hydrosilane described by formula

where R is as previously described, $b=0$ to 3, and $c=1$ to 4 with an effective amount of an alumina-zirconia cogel to effect formation of a mixture having reduced chlorocarbon content.

Contacting the mixture comprising as a major portion an organochlorosilane and as a minor portion a chlorocarbon and a hydrosilane with an alumina-zirconia cogel can be conducted in standard reactors for contacting liquids and gases with a heterogeneous catalyst. The process can be run as a continuous, semi-continuous, or batch process. Preferred is when the process is run as a continuous process using a packed-bed of alumina-zirconia cogel as a catalyst.

The organochlorosilanes present in the process can be part of the direct process crude mixture. By "direct process crude mixture", it is meant a mixture comprising as a major portion an organochlorosilane and as a minor portion chlorocarbons and hydrosilanes. In the direct process, methyl chloride is reacted with silicon in the presence of a copper catalyst to produce what is known as "direct process crude mixture". The organochlorosilane major portion in the direct process crude mixture may contain as much as 75 to greater than 99 weight percent of the desired organochlorosilanes.

The organochlorosilanes useful in the process are described by formula $$R_aSiCl_{4-a},$$

where each R is an independently selected hydrocarbon comprising one to about 20 carbon atoms and a=0 to 4. R can be, for example, an alkyl such as methyl, ethyl, propyl, isopropyl, butyl, sec-butyl, tert-butyl, pentyl, hexyl, heptyl, octyl, nonyl, undecyl and dodecyl; a cycloalkyl such as cyclopropyl, cyclobutyl, cyclopentyl, cyclohexyl, cycloheptyl and cyclooctyl; an alkenyl such as pentenyl, hexenyl, heptenyl, octenyl, vinyl and allyl; a cycloalkenyl such as cyclobutenyl, cyclopentenyl, cyclohexenyl, cycloheptenyl, and cyclooctenyl; an aryl such as phenyl, tolyl, and naphthyl; and an arylalkyl such as benzyl beta-phenylethyl and gamma-tolypropyl. The organochlorosilanes that may be reduced in chlorocarbon content can be, for example, trimethylchlorosilane, dimethyldichlorosilane, methyltrichlorosilane, triethylchlorosilane, diethyldichlorosilane, methylethyldichlorosilane, n-propyltrichlorosilane, ethylmethyldichlorosilane, and tert-butyldimethylchlorosilane. The preferred organochlorosilanes are those containing ethyl and methyl.

The present mixture comprises a chlorocarbon minor portion and a hydrosilane minor portion. The chlorocarbon minor portion is typically present at concentrations of 10 parts per million on a weight basis up to 1 to 2 weight percent of the mixture. When the mixture is contacted with the alumina-zirconia cogel, the chlorocarbon reacts with the hydrosilane to form the corresponding hydrocarbon and a chlorosilane in which SiH functionality is converted to SiCl. This hydrocarbon usually has a lower boiling point than the desired organochlorosilane and can be easily separated from the organochlorosilane resulting in a reduced chlorocarbon content in the organochlorosilane.

The chlorocarbons that can be reduced by the present invention can be, for example, 2-chloropropane, 1-chlorobutane, 2-chlorobutane, 2-chloro-2-methylpropane, 1-chloropentane, 2-chloropentane, 2-chloro-2-methylbutane, 1-chloropentane, 2-chlorohexane, 3-chlorohexane, 3-chloro-2-methylpentane, 2-chloro-2,3-dimethylbutane, 3-chlorooctane, and 2-chlorodecane.

The hydrosilanes useful in the present invention are described by formula $$R_bH_cSiCl_{4-b-c},$$

where R is as previously described, b=0 to 3, and c=1 to 4. The hydrosilane can be, for example, dichlorosilane, dimethylsilane, methylchlorosilane, methyldichlorosilane, dimethylchlorosilane, and trimethylsilane.

In order to maximize the conversion of chlorocarbon to hydrocarbon, the hydrosilane should be present in the mixture at a concentration producing a molar concentration of hydrogen atoms attached to silicon relative to the chlorocarbon of at least stoichiometrically equivalence and preferably greater than 1000 to 2000 percent stoichiometrically. A greater hydrosilane stoichiometric excess may be utilized, however no additional benefit is expected. When the mixture to be reduced in chlorocarbon content is a direct process crude mixture the hydrosilane may be present in the mixture as a product of the direct process and it necessary additional hydrosilane may be added to the mixture to provide a sufficient molar concentration of hydrogen atoms bonded to silicon.

The alumina-zirconia cogel catalyst useful in the present invention can be prepared by, for example, dissolving zirconium oxynitrate and alumina in water or an organic solvent such as alcohol to form a mixture. The mixture then may be coprecipitated using a weak base such as ammonium hydroxide. The mixture is washed, filtered, dried and calcined in a hot air oven at 500° C. to produce an alumina-zirconia composite metal oxide. By the term "cogel" it is meant that the catalyst has two components, an alumina component and a zirconia component.

The amount of alumina to zirconia in the alumina-zirconia cogel can be 1 to less than 100 weight percent. Preferable the amount of alumina to zirconia in the cogel is in the range of about 10 to 90 weight percent. More preferred the amount of alumina to zirconia in the cogel is in range of about 30 to about 70 weight percent. The most preferred amount of alumina to zirconia in the cogel is in the range of about 40 to 60 weight percent.

The physical form of the alumina-zirconia cogel is not critical and can be, for example, powder, granule, pellet, tablet, lump, or extrudate. The form of the alumina-zirconia cogel will depend on the required reactor column throughput. It is preferred that the alumina-zirconia cogel be in granule, tablet, or extrudate form. When the alumina-zirconia cogel is granules a preferred size is 10 to 15 mesh. Preferred is when the granules have a size of 12 to 15 mesh. It is desirable that the BET surface area of the alumina-zirconia cogel is in a range of about 100 to 350 m²/g. The preferred BET surface area is about 150 to about 250 m²/g.

The present mixture is contacted with an effective amount of an alumina-zirconia cogel. By effective amount it is meant enough to reduce the chlorocarbon content in the mixture. The alumina-zirconia cogel concentration relative to the chlorocarbon concentration of the mixture is not critical to the operation of the process. However, the alumina-zirconia cogel concentration will affect the length of time required to achieve the desired reduction in chlorocarbon content. Thus, a packed column in which the reactants contact a large surface area of catalyst in a short period of time is preferred. An example of a useful reactant to catalyst ratio and through-put rate is provided in the examples herein.

The chlorocarbon reduction effectiveness of the present process is a function of both the temperature at which the mixture is contacted with the alumina-zirconia cogel and the contact time length. The contact temperature can be in the range of about 25° C. to 200° C. Preferred is a contact temperature in the range of about 55° C. to 120° C. Most preferred is a contact temperature in the range of about 80° C. to 90° C.

The contact time required to reduce the chlorocarbon contacting the mixture also depends upon the contact temperature. In general, the higher the contact temperature the shorter the required contact time. A useful contact time for the mixture with the alumina-zirconia cogel is in the range of about five seconds to 20 minutes. Most preferred is a contact time of about 30 seconds to 5 minutes at a contact temperature in the range of about 80° C. to 90° C.

Separating the alumina-zirconia cogel catalyst from the organochlorosilane and hydrocarbon can be effected by conventional means. When the process is operated in a batch mode or a continuous mode in a stirred-tank reactor, the catalyst can be separated by such means as a settling tank, filtration, or a combination thereof. When a packed bed of catalyst is used in a continuous mode, the bulk of the catalyst will be retained in the packed bed. Any catalyst fines not held in the packed bed can be removed by conventional methods such as settling or filtration. The hydrocarbon can be separated from the organohalosilane by any conventional methods for separating liquid mixtures. Distillation is the preferred means for separating the hydrocarbon from the organochlorosilane.

The following example is provided to illustrate the present invention. This example is not intended to limit the scope of the claims herein. Example 1. A nitrate salt mixture was prepared by dissolving zirconium oxynitrate (250 gm), and aluminum nitrate (250 gm) in 1500 ml of deionized water. The nitrate salt mixture was added to 2 liters of deionized water, adjusted to pH 8 with ammonium hydroxide, over a one hour period with rapid stirring to form a gelled mixture. The gelled mixture was stirred an additional 6 hours and allowed to sit for two days. The gelled mixture was washed twice with deionized water. The gelled mixture was dried for 24 hours at 110° C. and then calcined in a hot air oven at 500° C. for 20 hours to produce an alumina-zirconia cogel (116 gm). The alumina content of this alumina-zirconia gel was 21 weight percent, and the specific surface area was 100 m²/g. During the calcining process the alumina-zirconia cogel was fractured and sieved to granules in the 12 to 15 mesh size range.

Different weight percent compositions of the alumina-zirconia cogel were prepared by the same method by varying the ratio of zirconium oxynitrate to aluminum nitrate. The control samples containing 100 weight percent alumina gel and 100 weight percent zirconia gel were prepared by the same method, but by omitting the zirconium oxynitrate and aluminum nitrate, respectively.

The Control Experiment was conducted with CS331-4 (0.3 dia. extrudates) purchased from United Catalysts, Louisville, Ky.

A direct process crude mixture sample comprising, as a major portion dimethyldichlorosilane resulting from the reaction of silicon with methyl chloride was spiked with 2442 ppm of isopropyl chloride. The sample also contained about two weight percent total of dimethylchlorosilane and methyldichlorosilane. The spiked sample was then passed through a 1.9 cm diameter by 20.3 cm diameter length column packed with the alumina-zirconia cogel at a temperature of 90° C. and a pressure of 414 kPa. The effluent from the column were analyzed by gas chromatography with a mass spectrometer detector (GC/MS) for the chlorocarbon content. The residence times were calculated assuming a 50 percent void volume for all gels and cogels.

Table 1 list the alumina-zirconia cogel compositional weight percent, and chlorocarbon reduction efficiencies at 1, 2, and 5 minute residence times.

TABLE 1

WEIGHT PERCENT CHLOROCARBON REDUCTION

| Catalyst Composition | | | Residence Time (minutes) wt. % Chlorocarbon Reduction | | |
|---|---|---|---|---|---|
| wt. % alumina | wt. % zirconia | Catalyst Form | 5 | 2 | 1 |
| 100 | 0 | +12 Mesh Granules | 93 | 86 | — |
| 82 | 18 | +12 Mesh Granules | 93 | 89 | — |
| 68 | 32 | +12 Mesh Granules | 94 | 91 | — |
| 44 | 56 | +12 Mesh Granules | 99 | 97 | 95 |
| 44 | 56 | +12 Mesh Granules | 99 | 99 | 99 |
| 44 | 56 | 0.3 cm × 0.3 cm Tablets | 99 | 86 | 55 |
| 44 | 56 | 0.3 cm Extrudates | 98 | 84 | 67 |
| 13.5 | 86.5 | +12 Mesh Granules | 96 | 95 | — |
| 0 | 100 | +12 Mesh Granules | 90 | 75 | — |
| CONTROL EXPERIMENT | | | | | |
| 100% Al₂O₃ (CS331-4) | | | 92 | 75 | 53 |

I claim:

1. A process for reducing chlorocarbon content of a mixture comprising an organochlorosilane, the process comprising contacting a mixture comprising as a major portion an organochlorosilane described by formula $$R_aSiCl_{4-a},$$

where each R is an independently selected hydrocarbon comprising one to about 20 carbon atoms and a=0 to 4 and as a minor portion a chlorocarbon and a hydrosilane described by formula $$R_bH_cSiCl_{4-b-c},$$

where R is as previously described, b=0 to 3, and c=1 to 4 with an effective amount of an alumina-zirconia cogel to effect formation of a mixture having reduced chlorocarbon content.

2. A process according to claim 1, where the alumina zirconia cogel comprises 1 to less than 100 weight percent alumina.

3. A process according to claim 1, where the alumina-zirconia cogel comprises about 10 to 90 weight percent alumina.

4. A process according to claim 1, where the alumina-zirconia cogel comprises about 30 to 70 weight percent alumina.

5. A process according to claim 1, where the alumina-zirconia cogel comprises about 40 to 60 weight percent alumina.

6. A process according to claim 1, where the mixture is contacted with the alumina-zirconia cogel at a temperature within the range of about 25° C. to 200° C.

7. A process according to claim 1, where the mixture is contacted with the alumina-zirconia cogel at a temperature within the range of about 55° C. to 120° C.

8. A process according to claim 1, where the mixture is contacted with the alumina-zirconia cogel at a temperature within the range of about 80° C. to 90° C.

9. A process according to claim 1, where the mixture is contacted with the alumina-zirconia cogel for a time period in the range of about five seconds to about 20 minutes.

10. A process according to claim 1, where the mixture is contacted with the alumina-zirconia cogel for a time period in the range of about 30 seconds to 5 minutes at a contact temperature in the range of about 80° C. to 90° C.

11. A process according to claim 1, where the process is run as a continuous process.

12. A process according to claim 1, where the process is run as a semi-continuous process.

13. A process according to claim 1, where the process is run as a batch process.

14. A process according to claim 1, where the surface area of the alumina-zirconia cogel is within the range of about 100 to 350 m²/g.

15. A process according to claim 1, where the surface area of the alumina-zirconia cogel is within the range of about 150 to 250 m²/g.

* * * * *